United States Patent
Lafitte et al.

(10) Patent No.: US 9,925,357 B2
(45) Date of Patent: Mar. 27, 2018

(54) ACCESS SHEATH

(71) Applicant: Coloplast A/S, Humlebaek (DK)

(72) Inventors: Mathieu Lafitte, Sainte Nathalene (FR); Laurent Pascal, Toulouse (FR)

(73) Assignee: Coloplast A/S, Humlebaek (DK)

( * ) Notice: Subject to any disclaimer, the term of this patent is extended or adjusted under 35 U.S.C. 154(b) by 51 days.

(21) Appl. No.: 14/205,443

(22) Filed: Mar. 12, 2014

(65) Prior Publication Data

US 2014/0276635 A1    Sep. 18, 2014

(30) Foreign Application Priority Data

Mar. 15, 2013    (EP) .................................... 13290063

(51) Int. Cl.
| | |
|---|---|
| *A61M 25/01* | (2006.01) |
| *A61M 25/06* | (2006.01) |
| *A61M 25/09* | (2006.01) |
| *A61B 17/34* | (2006.01) |

(52) U.S. Cl.
CPC .... *A61M 25/0172* (2013.01); *A61M 25/0169* (2013.01); *A61B 17/3478* (2013.01); *A61M 25/0668* (2013.01); *A61M 25/0905* (2013.01); *A61M 25/09041* (2013.01); *A61M 2025/018* (2013.01); *A61M 2025/0188* (2013.01); *A61M 2025/0681* (2013.01)

(58) Field of Classification Search
CPC .......... A61M 25/0169; A61M 25/0172; A61M 2025/018; A61M 2025/0188; A61M 2025/0681; A61M 25/0905; A61M 2025/0004; A61M 25/0017; A61M 2025/0175; A61M 25/0668; A61M 25/09041; A61M 2025/09125
See application file for complete search history.

(56) References Cited

U.S. PATENT DOCUMENTS

| | | | |
|---|---|---|---|
| 4,928,693 | A | 5/1990 | Goodin et al. |
| 5,478,328 | A | 12/1995 | Silverman et al. |
| 5,507,807 | A | 4/1996 | Shippert |
| 5,733,260 | A | 3/1998 | DeMaio |
| 5,765,682 | A | 6/1998 | Bley et al. |
| 6,007,517 | A | 12/1999 | Anderson |

(Continued)

FOREIGN PATENT DOCUMENTS

| | | |
|---|---|---|
| EP | 1660165 A1 | 5/2006 |
| GB | 2205751 | 12/1988 |
| WO | 2009127216 | 10/2009 |

OTHER PUBLICATIONS

Office Action dated Jun. 6, 2013 in U.S. Appl. No. 12/144,688.
Office Action dated Jun. 7, 2013 in U.S. Appl. No. 13/765,997.
Dffice Action dated Nov. 15, 2013 in U.S. Appl. No. 13765997.

*Primary Examiner* — Shefali Patel
(74) *Attorney, Agent, or Firm* — Coloplast Corp., Coloplast A/S; Nick Baumann

(57) ABSTRACT

Disclosed is an assembly of parts for an endourological procedure, including a tubular sheath and an introducer, the tubular sheath being removably mounted on the introducer. The introducer comprises a security channel that is openable to shift a guidewire from a position inside the security channel to a position outside and next to the tubular sheath. Disclosed are also access sheaths and a method of performing an endourological procedure.

14 Claims, 4 Drawing Sheets

(56) References Cited

U.S. PATENT DOCUMENTS

| | | | |
|---|---|---|---|
| 6,095,990 A * | 8/2000 | Parodi | A61M 25/0172 600/585 |
| 6,471,684 B2 | 10/2002 | Dulak et al. | |
| 6,746,442 B2 | 6/2004 | Agro et al. | |
| 6,827,731 B2 | 12/2004 | Armstrong et al. | |
| 7,179,252 B2 | 2/2007 | Agro et al. | |
| 7,534,223 B2 * | 5/2009 | Boutilette | A61M 25/0029 600/434 |
| 7,637,863 B2 | 12/2009 | Deal et al. | |
| 7,909,811 B2 | 3/2011 | Agro et al. | |
| 7,967,830 B2 | 6/2011 | Ayala et al. | |
| 8,206,320 B2 | 6/2012 | Deal et al. | |
| 8,211,087 B2 | 7/2012 | Carter et al. | |
| 8,328,837 B2 * | 12/2012 | Binmoeller | A61B 1/018 604/164.01 |
| 2004/0143286 A1 * | 7/2004 | Johnson | A61F 2/856 606/194 |
| 2005/0059890 A1 | 3/2005 | Deal et al. | |
| 2005/0059990 A1 | 3/2005 | Ayala et al. | |
| 2005/0070794 A1 | 3/2005 | Deal et al. | |
| 2005/0070821 A1 | 3/2005 | Deal et al. | |
| 2005/0090835 A1 | 4/2005 | Deal et al. | |
| 2005/0143770 A1 | 6/2005 | Carter et al. | |
| 2006/0030864 A1 | 2/2006 | Kennedy, II et al. | |
| 2006/0195117 A1 | 8/2006 | Rucker et al. | |
| 2007/0149948 A1 | 6/2007 | Agro et al. | |
| 2007/0250001 A1 | 10/2007 | Hilaire et al. | |
| 2007/0276466 A1 | 11/2007 | Lavelle et al. | |
| 2009/0062769 A1 | 3/2009 | Graves | |
| 2009/0318894 A1 * | 12/2009 | Lafitte | A61M 25/0668 604/528 |
| 2011/0087234 A1 | 4/2011 | Ayala et al. | |

\* cited by examiner

ACCESS SHEATH

The invention relates to access sheaths through which surgeons can make an intervention with one or more tools within the human body. More particularly, the invention relates to an assembly of parts for an endourological procedure and to a method for carrying out an endourological procedure using the assembly of parts.

BACKGROUND

If a surgeon needs to access a kidney in a patient, e.g. in order to remove a kidney stone, and if a direct surgical intervention has been dismissed, the natural route of entry is as follows: going through the urethra into the bladder, passing the bladder, going beyond the ureteral meatus and then going through the ureter to reach the kidney.

The positioning of an access sheath has traditionally been performed by a quite restrictive method explained below.

Following the insertion of an endoscope into the bladder to locate the ureteral meatus, a first radiopaque guidewire is driven up to the bladder and then, with the aid of the endoscope targeting the ureteral meatus for introduction of the first guidewire into the ureter.

After the first guidewire has been set up, a radiopaque double channel ureteral probe is engaged by one of its both channels onto the first guidewire and it is driven up to the ureter. Through the other channel of the ureteral probe, a second guidewire is introduced until it too reaches the ureter. Then the ureteral probe is removed to leave the first and the second guidewires in the patient, one guide now functioning as a working guidewire and the other one functioning as a security guidewire. The security guidewire is then fixed to, and held in place on, the patient. During these first steps the radiopaque components have been visualized to check their positions by means of an X-ray cannon connected to a monitor.

The access sheath to be positioned sits on, or is threaded onto, an introducer element projecting proximally beyond the access sheath, the introducer comprising a channel. The access sheath on the introducer is then guided onto the working guidewire through the channel and the sheath is then driven up to a position between the bladder and the kidney, however relatively nearer to the bladder. The introducer element and the working guidewire are then removed to leave behind in place only the access sheath, and near it, the security guidewire that can be used in case of unforeseen difficulties.

The course of all these steps of positioning the access sheath highlights the fundamental problem behind the present invention: reducing the number of positioning steps in order to save time and reduce the risks for the patient involved with the procedure while limiting the number of necessary components (including the working and security guidewires, the ureteral probe for positioning the security guidewire and the dilator element).

WO2009/127216A1 relates to a catheter for positioning an access sheath and a security guide next to the sheath for an intervention in a difficult-to-access area within the body, comprising, along the catheter, at least one security channel for positioning a guide, characterised by the fact that the security channel is a channel extending between an outer hole and an inner hole, the wall of the catheter extending between both holes of the security channel being arranged to open under the action of a peel strength directed from inside to outside the channel.

SUMMARY OF THE INVENTION

The present invention relates to access sheaths to aid surgeons in performing certain endoscope-assisted surgical procedures, i.e. procedures being performed inside the body of a patient by means of a scope being connected to a monitor allowing the surgeon to see the site of interaction. The access sheaths may be especially useful in an endourological procedure however the present application is also intended to embrace the use of the invention in other procedures where suitable. Particularly, the invention relates to an assembly of parts facilitating the use of a single guidewire, contrary to hitherto known procedures requiring both a working guidewire and a security guidewire thus meaning that less insertions and retractions of surgical devices to and from the patient are needed. More particularly, the invention is about facilitating smooth and easy disengagement of a guidewire from the access sheath when the access sheath has been inserted into the patient's body.

DETAILED DESCRIPTION OF THE INVENTION

Figure 1:
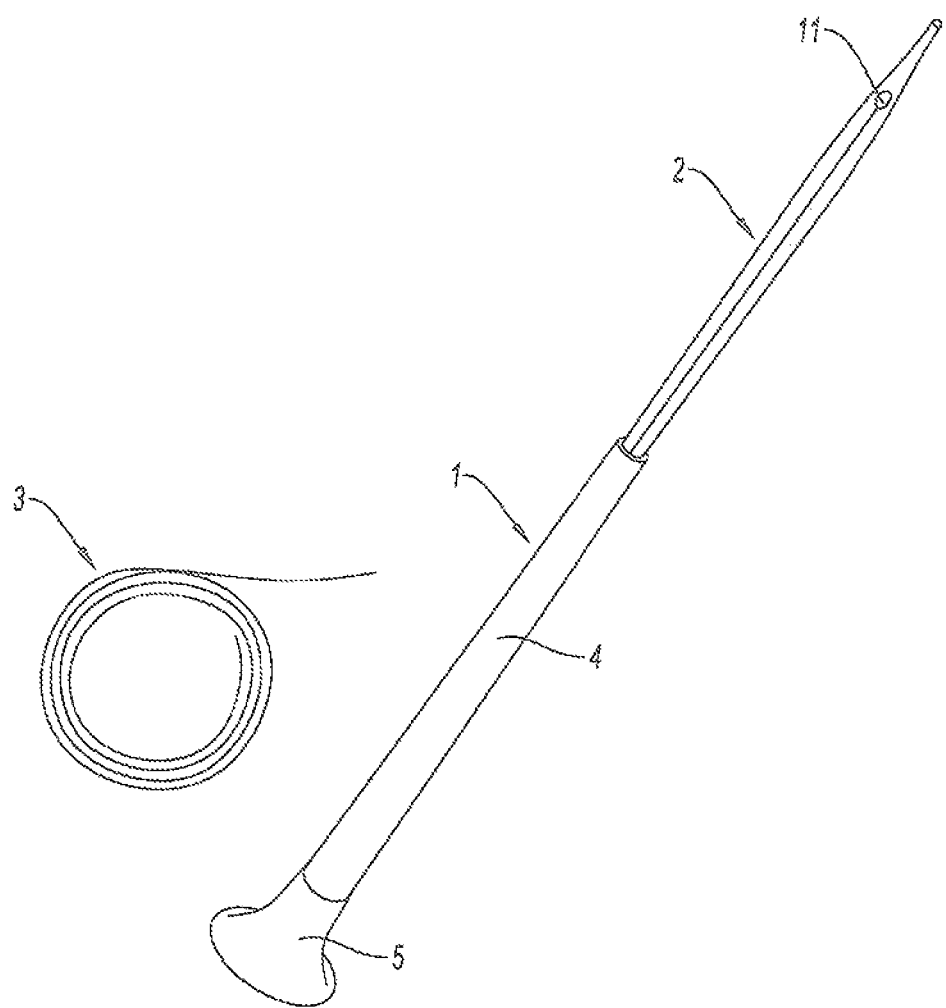
FIG. 1 is a perspective view of the assembly of parts according to the invention comprising an elongate tubular sheath mounted on an elongate introducer also showing a guidewire.

In the following, whenever referring to a proximal end of an element of the invention, the referral is to the end adapted for being inserted first into the patient. Whenever referring to the distal end of an element, the referral is to the end opposite the insertion end. In other words, the proximal end is the end closest to (or inside the body of) the user, when the element is to be (or is) inserted and the distal end is the opposite end—for some elements of the invention the distal end is located externally of the user's body when it is used.

Furthermore, when referring to a tapered end of an element, this may include and be seen as a frustoconical shape of the end of the element.

The longitudinal direction is the direction from the distal to the proximal end. The transverse direction is the direction perpendicular to the longitudinal direction, which corresponds to the direction across the shaft of the element.

In a first aspect, the invention relates to an assembly of parts for an endourological procedure comprising an elongate introducer and an elongate tubular sheath removably engaged onto the introducer, the elongate tubular sheath comprising at least one lumen extending between a proximal end and a distal end thereof, the elongate introducer comprising at least one security channel along at least a part of its longitudinal extent defined between a tapered proximal end and a distal end, the security channel adapted to accommodate a single guidewire during insertion of the assembly into the body of a patient, the security channel extending between a proximal hole and a distal hole in the introducer, a wall section of the introducer extending between the holes being arranged to open under the action of a radially outward directed force, wherein the security channel comprises controllable ejecting means adapted to externalize the single guidewire from the security channel upon activation.

According to the invention the assembly of parts is used to position the tubular sheath in the urinary tract of the patient, the tubular sheath thus functioning as an access sheath, and also to position a required security (or safety) wire outside and next to the tubular sheath for performing an endourological procedure. As the wall section of the elongate introducer is arranged to open under the action of a radially outward directed force (the direction of "radially outward" to be understood in relation to a central longitudinal axis of the elongate introducer), only a single guidewire is necessary.

Furthermore, by incorporating and employing controllable ejecting means for externalizing the guidewire from the security channel a smooth and reliable shifting of the position of the guidewire from inside the security channel to outside the introducer is ensured. This further has the advantage that less applied force is needed to externalize the guidewire from the introducer which in turn reduces stresses applied to the material of the guidewire, such guidewires often being delicate instruments of very small diameter.

When reference is made to "controllable" ejecting means, it is to be understood that controlling the activation of such ejecting means may be performed by the surgeon or assisting personnel via a control unit or similar located externally of the body of the patient. If considered suitable, such a control unit may form part of the assembly of parts according to the invention so as to be located at a practical and easily accessible position for the surgeon. However, and alternatively, the ejecting means may be configured to be controllable by virtue of the choice of materials and construction of the ejecting means, thus not necessarily requiring direct human interaction to be activated.

The tubular sheath may comprise one or more reinforcing elements embedded in its wall along at least a part of the longitudinal extent of the sheath, such as a coiled thread. Such reinforced tube defining the tubular sheath may thus be flexible, but resistant to collapse, compression and application. By way of example, but not exclusively, such reinforcing element may be provided in order to avoid kinking and/or twisting of the assembly during insertion into the body of the patient.

The openable wall section of the security channel may comprise a slit between the proximal and distal holes, lips of the slit being contiguous or overlapping each other when no forces are working on the introducer (rest state). Alternatively, the wall section of the security channel may have a breaking or perforation line between the proximal and distal holes to ease a splitting thereof to achieve its openability.

In embodiments, where the introducer has one security channel, the channel is named so because it serves for aiding the insertion of a security guidewire into the urinary tract. However, during the positioning of the assembly, it may be said to function especially as a working channel.

The security channel can extend along the entire length of the introducer, but the guidewire may exit the security channel through a distal hole not necessarily located at the distal-most end of the introducer. Instead the distal hole may be in a suitable location along the longitudinal extent of the introducer.

In embodiments, the controllable ejecting means is located radially closer to a central longitudinal axis of the introducer than the accommodated guidewire.

According to such embodiments, the ejecting means are consequently placed in a position where the accommodated guidewire will be ejected, or externalized, radially away from the central longitudinal axis of the introducer, through the openable wall section of the security channel when the ejecting means is activated. Activation of the ejecting means will cause a radially outward directed force to work on the guidewire of a pre-determined sufficient magnitude to ensure opening of the wall section of the security channel. More than one ejecting means may be comprised in the security channel or, in the case of more than one security channel being employed, one or more ejecting means may be employed for each of those security channels.

In embodiments, the controllable ejecting means is an expandable element.

The expandable element may by way of examples, but not exclusively, expand by filling an inner hollow volume thereof with a fluid media or by comprising a material that swells as a consequence of fluid or moisture uptake. The construction and material choices for the expandable element may be configured to expand the element at a pre-determined rate. As an example, this may be employed by configuring the element with a highly absorbing, highly swellable material in a core part surrounded and/or enclosed by a somewhat less absorbing and swellable material provided as a mantle part. During the procedure in which the assembly of parts is used, a fluid is continuously injected into the urinary tract in order to keep the channels of the urinary tract expanded i.a. to allow best possible passage of instruments and tools and to increase visibility. Due to the relatively constantly fluid-filled surroundings, a swellable expandable member according to the above example may expand at a pre-determined rate and thus externalize the guidewire once swelled to a desired extent.

In embodiments, the expandable element is an inflatable member.

The inflatable member may comprise a medical grade silicone balloon adapted to be expanded by injection of a fluid thereinto. Other types of materials may be used for such a balloon just as the specific shape of the balloon may be adapted, particularly to the shape and size of the security channel.

In embodiments, the expandable element is in communication with a fluid reservoir.

The fluid reservoir may preferably, but not exclusively, be located outside the patient's body. The communication between the expandable element and the fluid reservoir may be effected via one of the parts of the assembly, particularly the elongate introducer, or alternatively through a separate, dedicated channel means.

In embodiments, the elongate introducer further comprises at least one passageway along at least a part of its longitudinal extent.

The passageway may be a fluid channel for injecting fluids such as saline (e.g. for dilation/expansion of the urinary tract as explained above) or X-ray contrasting fluid into the area of intervention during the procedure. The passageway may communicate with one or more fluid inlet/outlet holes at or near the proximal end of the introducer. The passageway and communicating holes may also function as means for draining excessive fluid material and/or bodily fluids from the patient out through a distal end of the introducer.

In embodiments, particularly the at least one passageway provides the communication between the expandable element and the fluid reservoir. Thereby, the fluid communication may be effected through such passageway without requiring any modification of the introducer and advantageously using the at least one passageway for more than one purpose which in turn frees space in the introducer that may be reserved for other applications or for downsizing the overall outer diameter of the introducer.

In embodiments, the security channel further comprises guidewire retention means adapted to securely retain the guidewire in place in the security channel during insertion of the assembly into the body of a patient.

This may reduce or even eliminate the risk of the guidewire being unintentionally externalized through the openable wall section of the security channel during insertion of the assembly by advancing the introducer via the guidewire.

Occasionally, during insertion of the assembly, the surgeon may experience that the proximal end of the introducer faces some resistance to the insertion and particular care has to be taken not to harm tissue. Despite being careful, such encountered resistance may cause a slight or moderate kinking or bending of the relatively soft (non-reinforced) proximal end of the introducer, which may in turn result in the openable wall section of the introducer opening at least partly, thereby increasing the risk of unintentional externalization of the guidewire.

The retention means may in principle comprise any means capable of keeping the guidewire securely positioned in the security channel during insertion and simultaneously being non-obstructive to the externalization of the guidewire upon activation of the ejecting means. Some non-limiting examples could be one or more magnets located in the security channel or simply a decrease in an internal cross-sectional distance between opposite walls of the security channel, or a decrease in diameter, in either case measured near the opening in the wall section of the security channel.

In embodiments, the proximal hole in the introducer is located in a proximal-most end of the introducer.

Thereby, the guidewire may be centered in relation to the longitudinal axis of the introducer which eases correct insertion into the correct location in the patient.

The assembly of parts according to the first aspect is used according to the following method constituting a second aspect of the present invention:

A method for positioning an elongate tubular sheath and a security guidewire next to the sheath in an endourological procedure using the assembly of parts according to the invention, comprising the steps of positioning a single guidewire in a desired position,
engaging, driving up and setting up the elongate introducer with the elongate tubular sheath removably threaded thereonto by passing the single guidewire through and along the security channel to a position where a tapered proximal end of the elongate introducer is placed just distal of the proximal end of the single guidewire,
opening the wall section of the elongate introducer by the action of a radially outward directed force caused by activation of the controllable ejecting means thereby externalizing the single guidewire to a position outside the elongate introducer, and
retracting the elongate introducer from the elongate tubular sheath leaving the single guidewire outside and next to the tubular sheath for functioning as a security wire.

According to the method, only one single guidewire is necessary. The single guidewire is initially used as the working guidewire for bringing the tubular sheath controllably into the correct position in the urinary tract. When it has been confirmed that the tubular sheath is placed correctly (by X-ray imaging), the ejecting means are activated thereby externalizing the single guidewire to a position outside the elongate introducer achieved as a smooth and reliable shifting of the position of the guidewire from inside the security channel to outside the introducer. By the present method, it is further achieved that less applied force is needed to externalize the guidewire and to subsequently retract or withdraw the introducer from the tubular sheath, because the externalization of the guidewire is not caused by the action of retracting the introducer distally out of the tubular sheath—instead the guidewire is readily externalized before retraction of the introducer, thereby easing withdrawal thereof from the tubular sheath.

According to the method, the single guidewire is shifted from being a working guidewire to being a security guidewire. Thereby, instead of having to use two individual guidewires, according to the invention only a single guidewire is necessary and the number of necessary components for the procedure is thus reduced.

In a third aspect, the invention relates to an access sheath comprising an elongate introducer and an elongate tubular sheath removably engaged onto the introducer, the elongate tubular sheath comprising at least one lumen extending between a proximal end and a distal end thereof,
the elongate introducer comprising at least one security channel along at least a part of its longitudinal extent defined between a tapered proximal end and a distal end, the security channel adapted to accommodate a single guidewire during insertion of the assembly into the body of a patient,
the security channel extending between a proximal hole and a distal hole in the introducer, a wall section of the introducer extending between the holes being arranged to open under the action of a radially outward directed force, wherein
the security channel comprises controllable ejecting means adapted to externalize the single guidewire from the security channel upon activation.

The access sheath according to the third aspect may provide similar benefits and be employed in a similar manner as described above with regard to the assembly of parts according to the first aspect, however it may be used to obtain the same benefits in other surgical procedures than endourology. A method for positioning an access sheath and a security guidewire next to the sheath in a surgical procedure using the access sheath according to the third aspect is therefore also envisaged.

The figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

The assembly of parts illustrated in FIG. 1 shows a tubular sheath 1 for accessing a place to be operated, for example the urinary tract. The tubular sheath 1 is formed of a reinforced tube 4 that is flexible, but resistant to collapse, compression and plication. The tubular sheath 1 is slid or mounted onto an introducer 2, configured to receive and accommodate at least one guidewire 3 during insertion of the assembly. A flared distal end, or bucket, 5, is also shown and is provided for easy introduction of instruments and tools.

Figure 2:
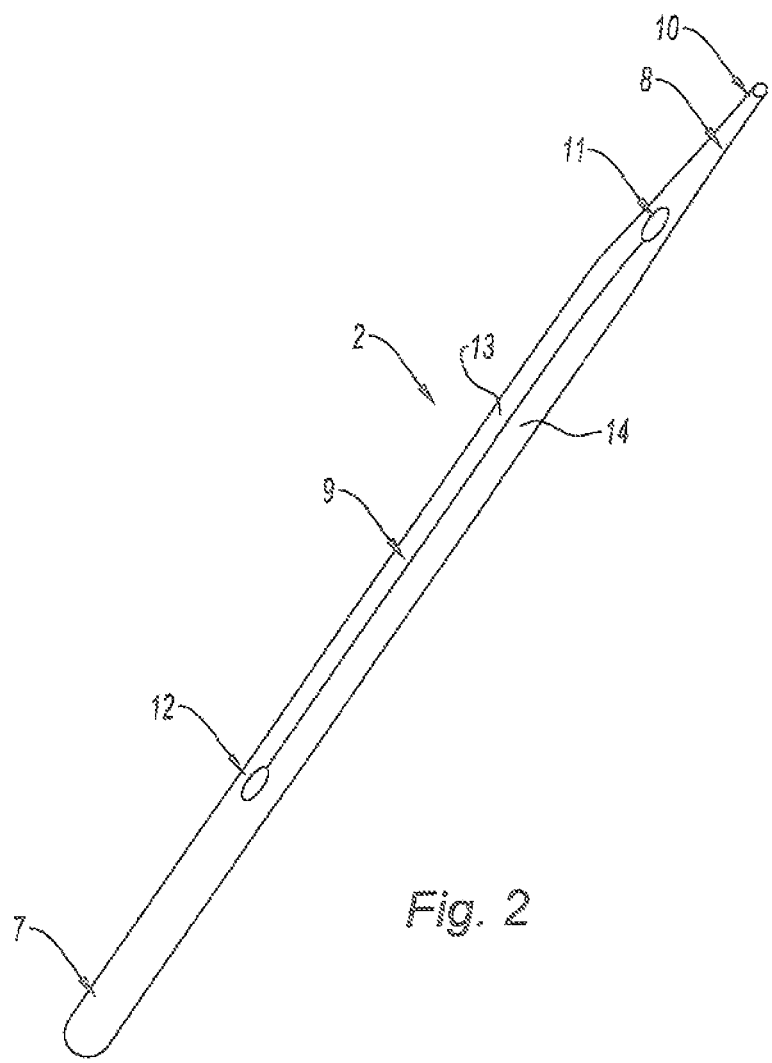
FIG. 2 is a perspective view of the elongate introducer.

The introducer 2 shown in more detail in FIG. 2 is a tube having two separate longitudinal hollow channels, or passageways, 61 and 62 which here both extend between a distal end 7 and a proximal end 8, the proximal end shown frustoconically, or tapered, shaped to facilitate its insertion into the patient. The proximal end 8 is shown narrowing towards the tip.

Figure 3:
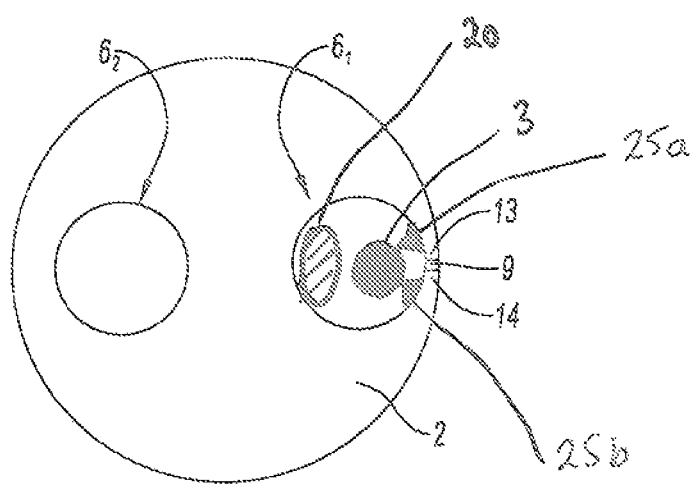
FIG. 3 is a cross-sectional view of the elongate introducer of FIGS. 1 and 2.

As shown in FIG. 3, channel 61 is a security channel and is shown with openable wall section as a slit 9 between two holes 11, 12 formed in the wall of the introducer 2. A proximal hole 11 is shown at the narrowed end part of the introducer, and a distal hole 12 approximately half way along the length of the introducer. The slit 9 of the openable wall section could extend along the entire length of the introducer, or just along a part of the length. At rest, lips 13, 14 of the slit 9 touch each other or may overlap.

FIG. 3 further illustrates a position of a controllable ejecting means, shown as a (non-inflated) inflatable balloon 20 that may be activated and thus inflated for externalization of the guidewire 3 through the openable wall section shown as slit 9. Retention means 25a and 25b provided in the security channel 61 for reducing any risk of unintentional externalization of the guidewire 3 during insertion of the assembly of parts is schematically shown as a decrease in diameter of the security channel, measured near the openable wall section slit 9.

Figure 4:
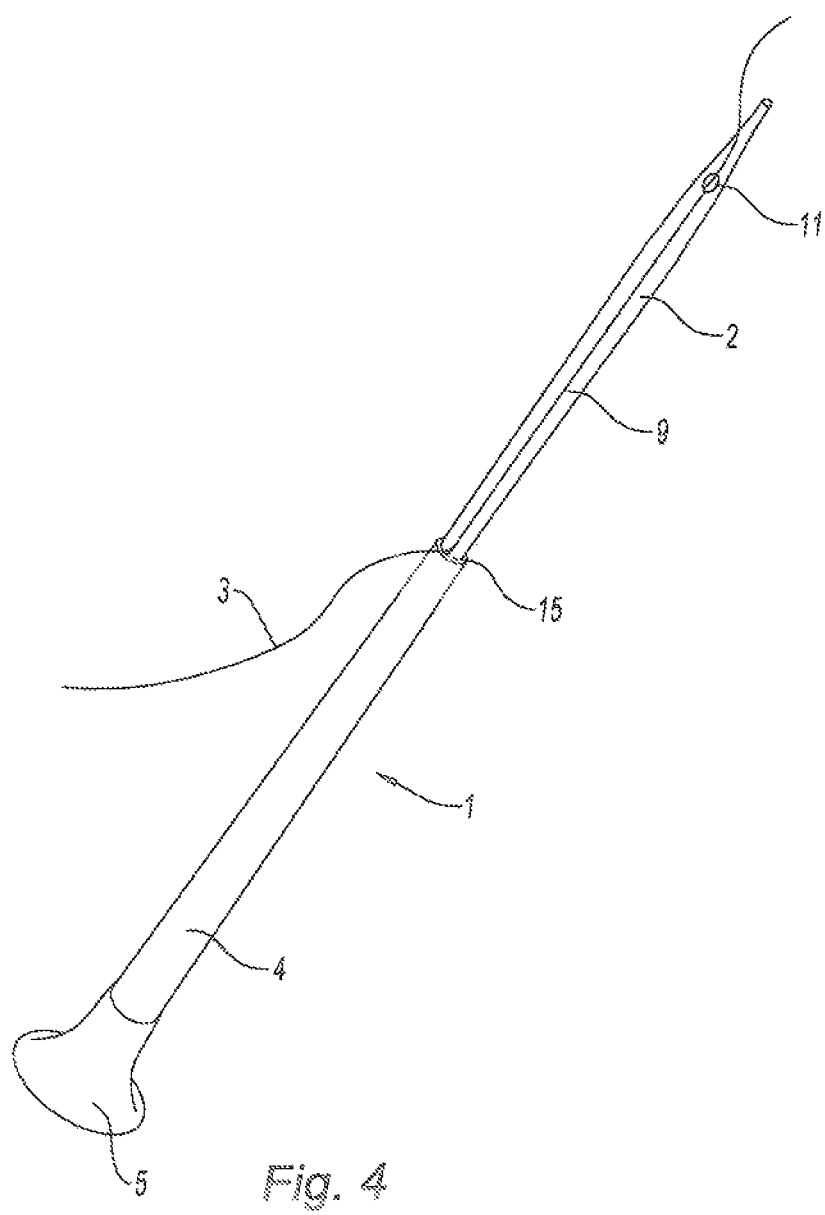
FIG. 4 is a perspective view of the assembly of parts comprising an elongate tubular sheath mounted on an elongate introducer being positioned on the guidewire.
Figure 5:
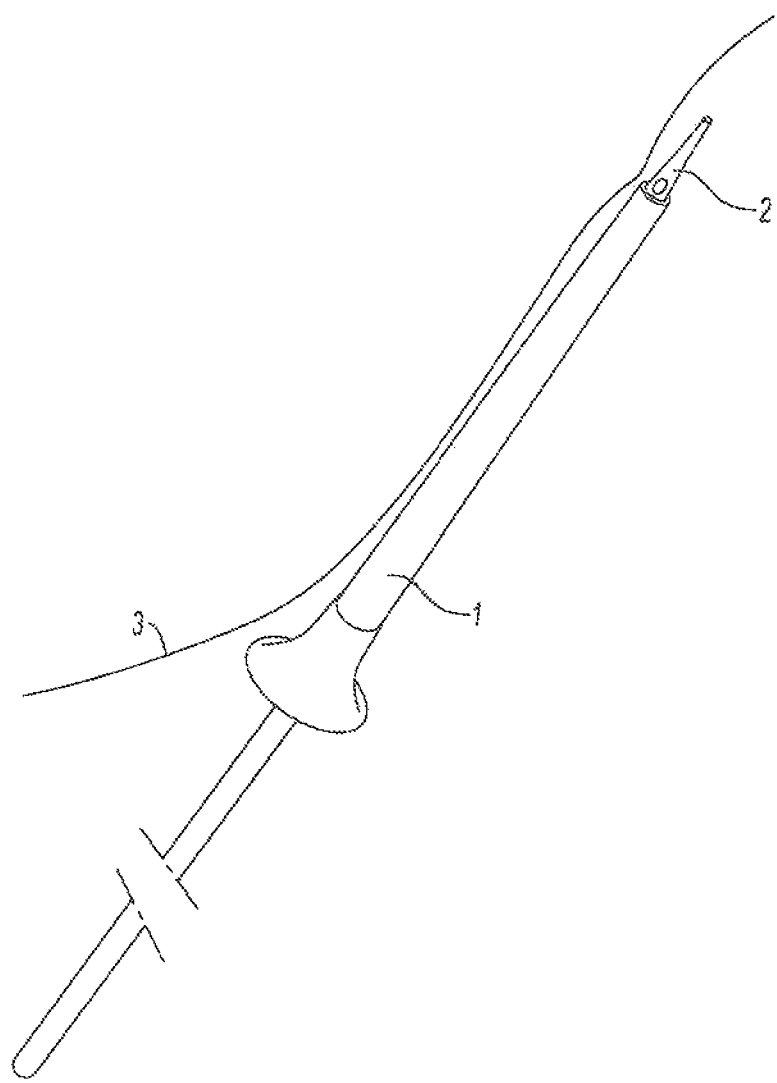
FIG. 5 is a perspective view of the assembly of parts of FIG. 4, the elongate introducer having been partly retracted from the tubular sheath and the externalized guidewire extending alongside the sheath.

FIG. 4 shows how the assembly of parts are inserted or introduced into the urinary tract via advancing the assembly in the proximal direction on the single guidewire 3, which will initially serve as a working guidewire before being converted to a security guidewire (FIG. 5).

After the guidewire 3 has been inserted in the ureter by introduction via the natural entry point, the introducer 2 is engaged on the guidewire 3 via the proximal hole 11 of the slit security channel 61 near the proximal end 8. By continuing to advance the introducer 2 along the guidewire 3, the end of the guidewire 3 emerges from the introducer via the distal hole 12, here shown at the middle of the introducer. The assembly of parts is advanced until the correct position in the patient's body is reached.

Subsequently, the ejecting means 20 of FIG. 3 is/are activated to externalize the guidewire as described, and following that step, the introducer 2 may be withdrawn from the tubular sheath 1 as indicated in FIG. 5.

What is claimed is:

1. An assembly of parts for an endourological procedure comprising an introducer and a tubular sheath removably engaged on the introducer,
    the tubular sheath comprising a lumen extending between a proximal end and a flared distal end of the tubular sheath,
    the introducer comprising a security channel along at least a part of a longitudinal extent defined between a tapered proximal end and a distal end, the security channel adapted to configure the introducer to accommodate a single guidewire during insertion of the assembly into a body of a patient,
    the security channel extending between a proximal hole and a distal hole of the introducer, a wall section of the introducer extending between the proximal and distal holes of the introducer that provides a slit that is arranged to open under action of a radially outwardly directed force, wherein
    the security channel comprises an ejector being inflatable to eject the single guidewire out of the slit and out of the introducer,
    wherein the security channel includes
    a first retainer disposed on one side of the slit; and
    a second retainer disposed on another side of the slit, the first and the second retainers being configured to avoid externalization of the single guidewire when the ejector is not inflated, the first and the second retainers being configured to decrease an inside diameter of the security channel as measured inside the security channel on either side of the slit.

2. The assembly according to claim 1, wherein the ejector is located radially closer to a central longitudinal axis of the introducer than the single guidewire.

3. The assembly according to claim 1, wherein the ejector comprises an expandable element configured to swell as a consequence of fluid or moisture uptake.

4. The assembly according to claim 3, wherein the expandable element comprises a fluid absorbing and swellable material.

5. The assembly according to claim 3, wherein the expandable element is in communication with a fluid reservoir.

6. The assembly according to claim 1, wherein the introducer further comprises a passageway formed along a length of the longitudinal extent.

7. The assembly according to claim 6, wherein the passageway provides a communication path for a fluid between an expandable element and a fluid reservoir.

8. The assembly according to claim 1, wherein the proximal hole in the introducer is located in a proximal-most end of the introducer.

9. The assembly according to claim 1, wherein
    a distance between the first retainer and the second retainer is shorter than a diameter of the single guidewire.

10. The assembly according to claim 1, wherein
    the first retainer protrudes radially inward toward a central longitudinal axis of the security channel; and
    the second retainer protrudes radially inward toward the central longitudinal axis of the security channel.

11. The assembly according to claim 1, wherein
    the first retainer and the second retainer are triangular in a cross-sectional view.

12. The assembly according to claim 1, wherein
    the first retainer and the second retainer are in contact with the single guidewire when the ejector is not inflated.

13. The assembly according to claim 1, wherein the ejector comprises a balloon configured to be expanded by injection of a fluid.

14. The assembly according to claim 1, the introducer comprising a passageway extending between the proximal end and the distal end of the introducer, wherein
    the passageway is separate from the security channel, the passageway is disposed radially across a central longitudinal axis of the introducer from the security channel, the passageway has a same radius as the security channel, and the passageway is circumferentially enclosed without a longitudinal slit.

* * * * *